United States Patent [19]

Escher et al.

[11] Patent Number: 5,443,754
[45] Date of Patent: Aug. 22, 1995

[54] PYRIDYLPYRIMIDINES, A PROCESS FOR THEIR PREPARATION AND THEIR USE IN LIQUID-CRYSTALLINE MIXTURES

[75] Inventors: Claus Escher, Mühltal; Gerhard Illian, Frankfurt am Main; Wolfgang Hemmerling, Sulzbach; Rainer Wingen, Hattersheim am Main, all of Germany

[73] Assignee: Hoechst Aktiengesellschaft, Frankfurt am Main, Germany

[21] Appl. No.: 64,024

[22] PCT Filed: Jan. 23, 1992

[86] PCT No.: PCT/EP92/00142

§ 371 Date: May 19, 1993

§ 102(e) Date: May 19, 1993

[87] PCT Pub. No.: WO92/12974

PCT Pub. Date: Aug. 6, 1992

[30] Foreign Application Priority Data

Jan. 24, 1991 [DE] Germany .................. 41 02 016.2

[51] Int. Cl.⁶ .................. G02F 1/13; C07D 213/53; C07D 239/02; C07D 401/04
[52] U.S. Cl. .................. 252/299.61; 544/298; 544/316; 544/333
[58] Field of Search .................. 252/299.61; 544/298, 544/316, 333

[56] References Cited

U.S. PATENT DOCUMENTS

| | | | |
|---|---|---|---|
| 4,668,425 | 5/1987 | Nigorikawa et al. | 252/299.61 |
| 4,713,197 | 12/1987 | Eidenschink et al. | 252/299.61 |
| 4,725,688 | 2/1988 | Taguchi et al. | 544/298 |
| 4,752,414 | 6/1988 | Eidenschink et al. | 252/299.61 |
| 4,765,924 | 8/1988 | Inoue et al. | 252/299.61 |
| 4,776,977 | 10/1988 | Taylor et al. | 252/314 |
| 4,804,759 | 2/1989 | Shibata et al. | 544/335 |
| 4,812,258 | 3/1989 | Krause et al. | 252/299.61 |
| 4,820,839 | 4/1989 | Krause et al. | 544/316 |
| 4,892,679 | 1/1990 | Blum et al. | 562/21 |
| 4,906,401 | 6/1990 | Dübal et al. | 252/299.61 |
| 4,906,752 | 6/1990 | Müller et al. | 544/318 |
| 4,952,335 | 8/1990 | Furukawa et al. | 252/299.61 |
| 5,286,410 | 2/1994 | Weber et al. | 252/299.61 |

FOREIGN PATENT DOCUMENTS

| | | |
|---|---|---|
| 0160790 | 11/1985 | European Pat. Off. . |
| 0240320 | 10/1987 | European Pat. Off. . |
| 0242716 | 10/1987 | European Pat. Off. . |
| 0391203 | 10/1990 | European Pat. Off. . |
| 4030603 | 4/1992 | Germany . |
| 61-280489 | 11/1986 | Japan . |

OTHER PUBLICATIONS

B. Kampa, K. D. Scherf and H. Zaschke, Preparation and Investigation of Liquid Crystalline "Bis-Pyrimidines", 7th Liquid Crystal Conference of Socialist Countries, 1987, Parduvice, CSFR, E8.

*Primary Examiner*—Mukund J. Shah
*Assistant Examiner*—Matthew V. Grumbling
*Attorney, Agent, or Firm*—Curtis, Morris & Safford

[57] ABSTRACT

A pyridylpyrimidine compound of the formula (I)

$$R^1-\underset{A-N}{\overset{(X^1)_n}{\underset{A=B}{\bigcirc}}}-\underset{C-D}{\overset{(X^2)_m}{\bigcirc}}-R^2 \quad (I)$$

in which
A is N and B is CH or A is CH and B is N
C is N and D is CH or C is CH and D is N,
$R^1$ is, for example, chiral or achiral alkyl having 1 to 16 carbon atoms,
$R^2$ is, for example, , $R^1$,
$X^1$, $X^2$ are F, Cl or CN, and
n, m are 0, 1 or 2, are components which are suitable for liquid-crystalline mixtures since they result in LC displays having favorable properties.

6 Claims, No Drawings

PYRIDYLPYRIMIDINES, A PROCESS FOR THEIR PREPARATION AND THEIR USE IN LIQUID-CRYSTALLINE MIXTURES

The unusual combination of anisotropic and fluid behavior of liquid crystals has led to their use in a large number of electrooptical switching and display devices. In these devices, their electrical, magnetic, elastic and/or thermal properties can be utilized for changes in orientation. Optical effect can then be achieved, for example, by means of birefringence, incorporation of dichroitically absorbing dyemolecules ("guest/host mode") or light scattering.

In order to satisfy the ever increasing demands in practice in the wide range of areas of application, there is a constant need for novel improved liquid crystal mixtures and thus also for a large number of mesogenic compounds of different structure. This is not only true of the areas in which nematic LC phases (for example TN="twisted nematic", STN="supertwisted nematic", SBE="supertwisted birefringence effect", ECB="electrically controlled birefringence") are used but also of those having smectic LC phases (for example ferroelectric and electroclinic ones). Many of the compounds suitable for LC mixtures can be described by a structuring principle (see, for example, J. Am. Chem. Soc. 108, 4736 (1986), structure I; Science 231, 350 (1986, FIG. 1 A; J. Am. Chem. Soc. 108,5210 (1986), FIG. 3) in which rings composed of cyclic compounds—aromatics, heteroaromatics, but also saturated ring systems—are linked to alkyl side chains which are straight-chain or substituted in the chain by small groups (for example methyl, chlorine) and thus are branched.

The use of pyrimidine compounds as components of liquid crystal mixtures is disclosed, for example, in U.S. Pat. Nos. 4,713,197, 4,725,688, 4,752,414, 4,765,924, 4,776,977, 4,804,759, 4,812,258, 4,820,839, 4,892,679, 4,906,401 and 4,906,752.

Similar pyridine compounds also to be used in liquid crystal mixtures are disclosed, for example, in EP-B 242,716, EP-B 240,320, EP-A 391,203, U.S. Pat. Nos. 4,765,924 and 4,952,335.

Liquid crystal mixtures containing pyridylpyrimidines of the formula (A) are described in JP-A 61280489 as compounds exhibiting nematic mesophases or exerting a favorable effect on nematic liquid crystal mixture.

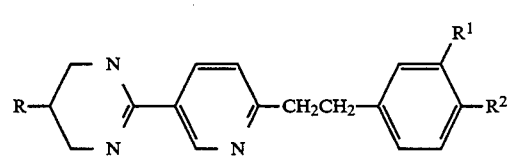

(R is $C_{1-10}$-alkyl or -alkyloxy; $R^1$ is H,Cl,F; $R^2$ is F,Cl,CN,$C_{1-10}$-alkyl or alkyloxy)

Pyrimidinylpyrimidines of the formula (B) were presented by B. Kampa, K. D. Scherf and H. Zaschke, (7th Liquid Crystal Conference of Socialist Countries, 1987, Parduvice, CSFR; E-8).

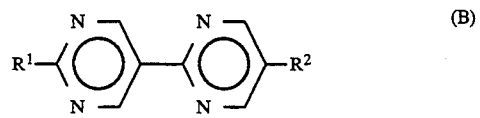

Binuclear representatives exhibit none or only a monotropic smectic phase, while trinuclear compounds exhibit $S_E$ and/or $S_A$ phases.

The object of the present invention is to provide novel mesogenic compounds which can be combined with other components to give LC mixtures having advantageous properties. This object is achieved by the compounds defined below:

Liquid-crystalline pyridylpyrimidine compounds of the formula (I)

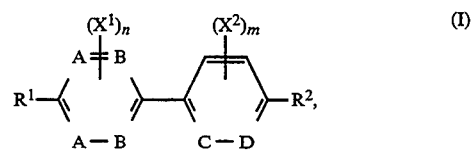

in which
A is N and B is CH or A is CH and B is N,
C is N and D is CH or C is CH and D is N,
$R^1$ is straight-chain or branched (chiral or achiral) alkyl having 1 to 16 carbon atoms or alkenyl having 2 to 16 carbon atoms, it also being possible for one or two non-adjacent —CH$_2$— groups to be replaced by —O—, —S—, —CO—, —CO—O—, —O—CO— or —O—CO—O— and it also being possible for one H to be replaced by F, or is one of the following radicals OCF$_3$, OCHF$_2$,

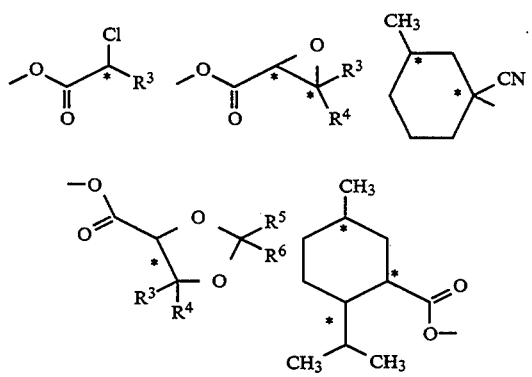

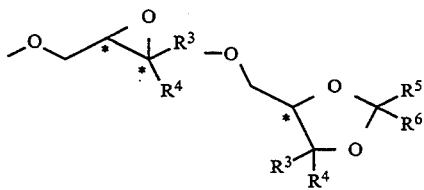

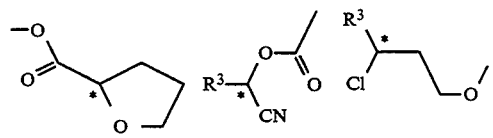

-continued

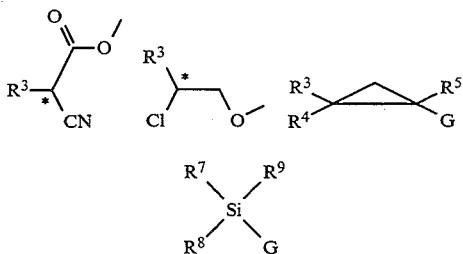

or R[10]—E—M—, with the proviso that if A is N, R[1] must not be linked with the pyrimidine via a —CO—O— or —O—CO—O— group, R[2] is identical to R[1], with the proviso that if D is N, the radicals R[1] linked to the pyridine ring via an —O—CO— or an —O—CO—O— group are excluded, X[1], X[2] are F, Cl, CN, preferably F, n,m, identical or different, are zero, 1 or 2, preferably zero, R[3], R[4], R[5], R[6] are H, straight-chain or branched alkyl having 1 to 16 carbon atoms or alkenyl with 2 to 16 carbon atoms, in which a —CH$_2$— group not adjacent to the linkage point can also be replaced by —O—, —CO—O— or —O—CO— or R[3] and R[4] or R[5] and R[6] together are cyclic alkyl having 3 to 8 carbon atoms, R[7], R[8], R[9] are straight-chain or branched alkyl having 1 to 16 carbon atoms or alkenyl having 2 to 16 carbon atoms, in which one or two non-adjacent —CH$_2$— groups can also be replaced by —O—, —CO—O— or —O—CO—, with the proviso that silicon is only bound to a carbon which has hydrogen and/or carbon as neighboring atoms, or are cyclic alkyl having 3 to 8 carbon atoms, or together with silicon can also be

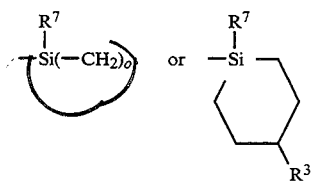

G is straight-chain or branched alkylene having 1 to 16 carbon atoms or alkenylene having 2 to 16 carbon atoms, in which one or two non-adjacent —CH$_2$— groups can also be replaced by —O—, —S—, —O—CO—, —CO—O—, —S—CO— or —CO—S—, with the proviso that silicon is only bound to a carbon atom which has hydrogen and/or carbon atoms as neighboring atoms, R[10] is identical to R[1] but is not R[10]—E—M and is not restricted by the abovementioned proviso, E is 1,4-phenylene in which 1 or 2 H can also be replaced by F, Cl and/or CN, trans-1,4-cyclohexylene in which 1 or 2 H can also be replaced by F, Cl, CN and/or CH$_3$, pyrazine-2,5-diyl, pyridazine-3,6-diyl, pyridine-2,5-diyl, pyrimidine-2,5-diyl, 1,3,4-thiadiazole-2,5-diyl, 1,3-dioxane-2,5-diyl or 1,3-dithiane-2,5-diyl; preferably 1,4-phenylene or 1,4-cyclohexylene, M is —CO—O—, —O—CO—, —CO—S—, —S—CO—, —CH$_2$—, —C≡C—, —CH=CH— or a single bond, o is an integer from 3 to 8.

Preference is given to those compounds in which R[1] and R[2], identical or different, are linear or branched alkyl, alkyloxy or alkyldimethylsilyalkyl(oxy) of the formula R[7]—Si(CH$_3$)$_2$—G or correspond to one of the optically active groups listed above. Furthermore, preference is given to compounds in which one of the two radicals R[1] or R[2] is trans-alkylcyclohexylcarbonyloxy.

Particular preference is given to pyridylpyrimidine compounds of the formulae (II) and (III) and (IIIa)

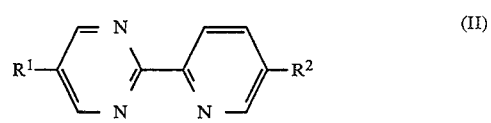

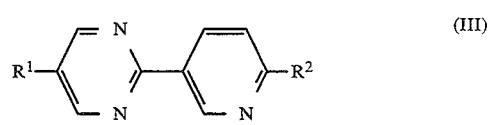

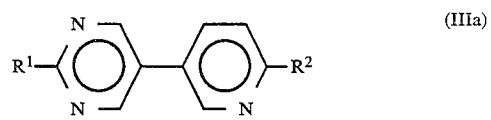

R[1] and R[2] having the abovementioned meaning.

The compounds according to the invention are particularly distinguished by the fact that they exhibit broad smectic C phase ranges and low melting points.

Moreover, in most cases, the compounds according to the invention also contain, apart from the additionally smectic C phases, smectic A phases, which are required in mixtures suitable for practical application for achieving good orientation.

They can be produced by standard reactions known per se, which in general involve reaction of a reactive pyridine derivative with a bifunctional electrophilic compound to give a pyrimidine system (condensation) for example by the route shown in scheme 1:

Scheme 1

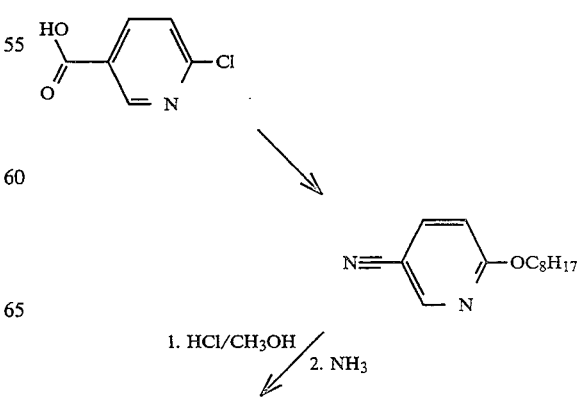

-continued
Scheme 1

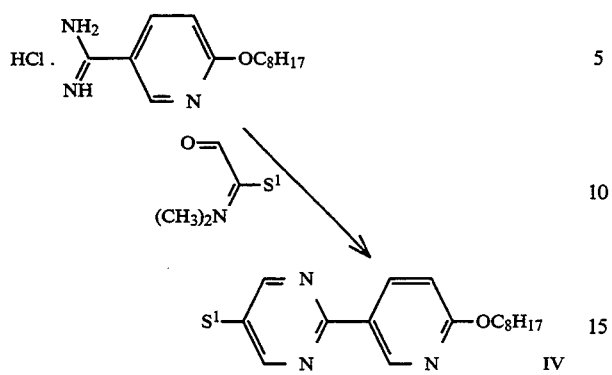

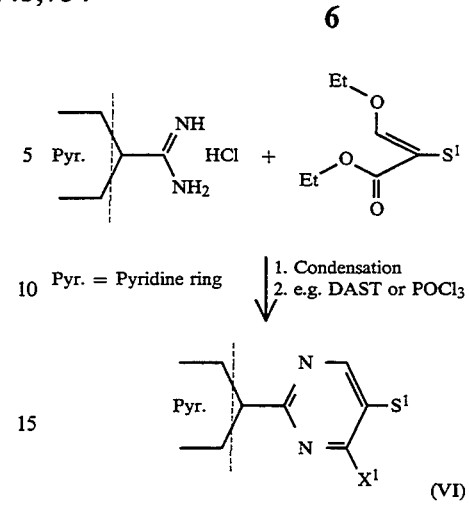

6-Chloronicotinic acid is converted in several steps to 6-octyloxynicotinonitrile. Amidine formation in the usual manner gives 6-octyloxynicotinamidine hydrochloride. Condensation with a dimethylaminoacroiein derivative leads to pyridylpyrimidine (IV), $S^1$ being $R^1$ or a protective group, such as benzyloxy, trialkylsilyloxy, tetrahydropyranyloxy, acyloxy, benzylthio or another suitable protective group listed in "T. W. Greene, Protective Groups in Organic Systems, Wiley (1981) or a hydroxy group. The protective groups can be cleaved off by the methods recommended in the same reference.

Pyridylpyrimidines of the formula (V) where $S^2$ is identical to or different from $S^1$ can be obtained, starting with, for example, 5-hydroxy-2-methylpyridine, which is first oxidized to the carboxylic acid. Continuation of the synthesis via nitrile and amidine takes place by customary methods [for example, H. Foerster and J. Walker, J.Chem.Soc. 1948, 1939 and H. Zaschke and H. Schubert, J. Prakt. Chem. 312, 494 (1970) and ibid. 315, 113 (1973)].

by condensing a pyridylamidine with a 2-(ethoxymethylene)carboxylic ester derivative, for example by the method of A. Boller et al. Z. Naturforsch. 33b, 433–438 (1978). The 4-hydroxy group on the pyrimidine ring can then be exchanged for chlorine or fluorine by reaction with $POCl_3$ or diethylaminosulfur trifluoride (DAST).

In order to obtain a compound where $X^1$ is CN, the hydroxy intermediate where $X^1$ is Br, which is produced analogously to the chloro compound, is reacted with copper cyanide in a suitable solvent such as N-methylpyrrolidone. Ethers of the formula (I) can, if the ether structure was not already present before formation of the heterocycle, be prepared from phenols of the formulae (IV), (V) or (VI) where $S^1$ or $S^2$ is OH or O-alkali metal by reaction with monofunctionally reactive alkyl halides or alkenyl halides or from monofunctionally reactive alcohols, such as derivable from the radicals listed under $R^1$, or from mesylates or tosylates thereof, the synthesis of these reaction components being assumed to be generally known.

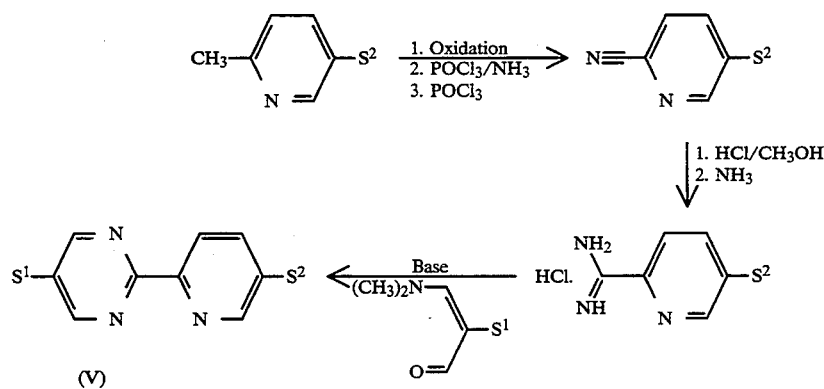

Compounds of the formula (VI) where $X^1$ is F or Cl can be synthesized as follows, Thus, for example, phenols or thiophenols of the formulae (IV), (V) or (VI) can be linked to hydroxy compounds in the presence of triphenylphosphine/azodicarboxylic diester (Mitsunobu reaction, for example in J. Chem. Soc. Perkin Trans. 1 1975, 461). The alkali metal salts or alkaline earth metal salts of these mesogenic hydroxy compounds or mercapto compounds produced separately or as intermediates can also be reacted with halogen compounds, toluene sulfonyloxy compounds or methylsulfonyloxy compounds (Williamson reaction, for example in Patai, The Chemistry of the Ether Linkage, Interscience Publishers, New York 1967, p. 446–468). Phenols or thiophenols of the formulae (II), (III) or (IV) can also be reacted with carboxylic acids such as derivable from $R^1$ under condensation conditions (for example, March, Advanced Organic Chemistry, 3rd Ed., Wiley Interscience, New York 1985, p. 240, 348–353) or under the conditions of the Williamson reaction to give esters or thioesters. Analogously, this is also possible using mesogenic carboxylic acids ($S^1/S^2$ is COOH) and the hydroxy compounds derived from $R^1$.

The compounds of the formula (I) can also be obtained by coupling, for example, 2-alkyl- or 2-alkoxy-5-pyridinyl boronic acids—prepared, for example, according to "Houben-Weyl, Methoden der Organischen Chemie (Methods of Organic Chemistry), vol. 13/3a, p. 635–647" or "Basil J. Wakefield, The Chemistry of Organolithium Compounds, Pergamon Press 1974—organometallically, for example according to Tetrahedron 28, 5093 (1987) or Mol. Cryst. Liq. Cryst. 204, 91 (1991) or J. Chem. Soc. Perkin Trans. II 1989, 2041.

The coupling of pyrimidine boronic acids with bromopyridine compounds by the essentially same methodology may also be possible.

The invention furthermore relates to a liquid-crystalline, in particular a ferroelectric, mixture comprising 2 to 20, preferably 2 to 15 components, the mixture containing at least one compound of the formula (II). The other constituents are preferably selected from the known compounds exhibiting nematic, cholesteric and-/or tilted smectic phases. These include, for example, Schiff bases, biphenyls, terphenyls, phenylcyclohexanes, cyclohexylbiphenyls, pyrimidines, cinnamic esters, cholesterol esters and polynuclear esters of p-alkylbenzoic acids having a polar end group.

The liquid crystal mixtures in general contain 0.1 to 70 mol %, preferably 0.5 to 50 mol %, in particular 1 to 40 mol %, of the compound(s) according to the invention.

Moreover, the invention relates to an electrooptical switching and display device containing baseplates, a liquid crystal medium, electrodes, at least one orientation layer and, if desired, polarizers and further auxiliaries, which device contains a mixture according to the invention as described above as the liquid crystal medium.

The spontaneous polarization $P_S$[nC/cm$^2$], optical response time $\tau$[$\mu$S] and effective switching angle $\Theta_{eff}$[°] values of the ferroelectric liquid crystal mixtures were determined as follows:

The $P_S$ values were measured by the method of H. Diamant et al. [Rev. Sci. Instr. 28, 30 (1957)] in which measurement cells having an electrode spacing of 2 $\mu$m and rubbed polyimide as the orientation layer are used. To determine T and $\Theta_{eff}$, the measurement cell is mounted on the revolving stage of a polarizing microscope between crossed analyzer and polarizer. The position of the stage at which light transmission is at a minimum for both switching states in the cell is determined by revolving the stage. The difference between the two positions on the revolving stage is twice the effective tilting angle. The switching time T is determined by means of a photodiode by measuring the rise time of the light signal from 10 to 90% of signal height. The switching voltage is composed of square pulses and is $\pm$10 V/$\mu$m. The phase transition temperatures are determined during heating by observing the changes in texture by means of a polarizing microscope. In contrast, the melting point was determined by means of a DSC instrument. The phase transition temperatures between the phases
    nematic (N or N*)
    smectic C ($S_C$ or $S_C$*)
    smectic A ($S_A$ or $S_A$*)
    crystalline (X or C)
are given in °C., these values being written between the phase designations in the phase sequence.

Example 1

Synthesis of 2-(6-octyloxypyrid-3-yl)-5-octyloxypyrimidine

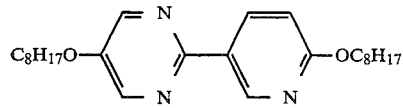

52 g (400 mmol) of octanol in 150 ml of dioxane are added dropwise to 12 g (400 mmol) of 80% NaH in 30 ml of dry dioxane at 70° C. After refluxing for 2 hours, 55 g (300 mmol) of ethyl 6-chloronicotinate in 1150 ml of dioxane are added dropwise, and the reaction solution is refluxed for another 5 hours. The solution is poured onto 400 ml of ice water, the phases are separated, and the aqueous phase is extracted several times with ether. The combined organic phases are washed with saturated common salt solution, dried over magnesium sulfate, and concentrated in vacuo. The product is purified by chromatography on silica gel.

55.8 g of 6-octyloxynicotinic ester are added to 500 ml of concentrated ammonia solution with stirring. The mixture is allowed to stand overnight, the precipitate is filtered off with suction and washed with a small amount of water. The mother liquor is evaporated to a large extent, as a result of which further product precipitates. It is recrystallized from water.

45 g (180 mmol) of 6-octyloxynicotinamide and 41.4 g (270 mmol) of phosphorus oxychloride are heated at 125° to 130° C. for 2 hours. The mixture is concentrated in vacuo, and the residue is covered with a layer of 250 ml of chloroform. 450 ml of concentrated sodium carbonate solution are added with vigorous stirring. After stirring for 10 minutes, the phases are separated, and the aqueous one is extracted several times with chloroform. The combined organic phases are washed with water, dried over magnesium sulfate and concentrated in vacuo. The crude product is purified by chromatography on silica gel. 21.8 g (100 mmol) of 6-octyloxynicotinonitrile and 6.42 g (200 mmol) of absolute methanol are initially introduced into 200 ml of dioxane. At 0° C., hydrogen chloride is introduced until saturation is reached. The mixture is allowed to stand at 0° C. overnight and then filtered on an inert gas. The precipitate is dried at 50° C. in vacuo over KOH. 30.1 g (100 mmol) of methyl 6-octyloxynicotinimidate suspended in 300 ml of EtOH are added to 110 ml of ethanol saturated at 20° C. with ammonia. The mixture is stirred at 60° C. for 2.5 hours and at room temperature overnight. The reaction solution is evaporated almost to dryness, and the residue is stirred with ether. The precipitate is filtered off with suction and dried in vacuo. 0.92 g (40 mmol) of Na are dissolved in 30 ml of ethanol. 5.46 g (24 mmol) of 2-octyloxy-3-dimethylaminoacrolein in 10 ml of ethanol are added dropwise at room temperature, and 5.7 g (20 mmol) of the 6-octyloxynicotinamidine hydrochloride are added in portions. The mixture is refluxed for 20 hours. The pH is adjusted to 3, the mixture is concentrated, taken up in 50 ml of water and extracted with dichloromethane. The organic phase is dried over magnesium sulfate and concentrated in vacuo. The end product is chromatographed on silica gel using dichloromethane and recrystallized from hexane. The product exhibits the following phase sequence: X 58 S$_C$60S$_A$95-.3I.

Example 2

Synthesis of (2S,3S)-3-butyloxiran-2-yl methyl 2-(6-octyloxypyrid-3-yl)pyrimidine-5-yl ether

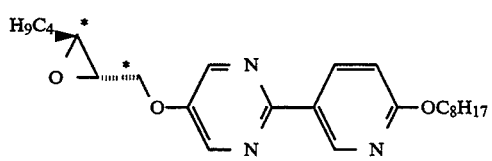

Preparation of the octyloxypyridinamidine hydrochloride and condensation with 2-benzyloxy-3-dimethylaminoacrolein are carried out analogously to Example 1.

1.96 g (5 mmol) of 5-benzyloxy-2-(6-octyloxypyrid-3-yl)pyrimidine are hydrogenated in 40 ml of THF in the presence of a spatula tip-full of para-toluenesulfonic acid and 200 mg of 10% palladium (on activated carbon). The mixture is filtered through Coriolite, concentrated in vacuo, taken up in 50 ml of dichloromethane and washed with 20 ml of water. The organic phase is dried over magnesium sulfate and concentrated in vacuo. The residue is recrystallized from petroleum ether. 1.36 g (4.5 mmol) of 5-hydroxy-2-(6-octyloxypyrid-3-yl)pyrimidine in 10 ml of DMF are added dropwise to 240 mg (8 mmol) of 80% NaH in 5 ml of DMF. 1.03 g (5 mmol) of (2S,3S)-3-butyloxiran-2-yl methyl methanesulfonate in 10 ml of DMF are then added, and the mixture is stirred at 60° C. for 1 hour. The reaction solution is hydrolyzed in 50 ml of saturated citric acid solution. The organic phase is separated off, and the aqueous one is extracted three times with dichloromethane. The combined organic phases are washed with water, dried over magnesium sulfate and concentrated in vacuo. The crude product is chromatographed on silica gel using dichloromethane and recrystallized from heptane. 1.1 g (60% yield). The pure product exhibits the following phase sequence:
X 72 (38S$_c$* 42) S$_A$* 105 I.
[α]$_D$= −16.6° (c=1.7, CHCl$_3$).

Example 3

Synthesis of 2-(6-octyloxypyridin-3-yl)pyrimidine-5-yl trans-4-pentylcyclohexanecarboxylate

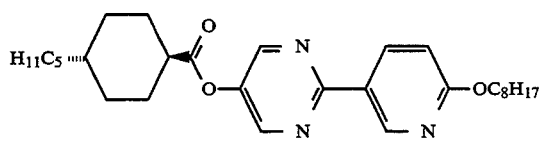

0.21 g (1 mmol) of trans-4-pentylcyclohexanecarboxylic acid, 0.30 g (1 mmol) of 5-hydroxy-2-(6-octyloxypyridin-3-yl)pyrimidine (for preparation see Example 2) and 0.01 g (0.1 mmol) of 4-dimethylaminopyridine are added to 0.21 g (1 mmol) of dicyclohexylcarbodiimide in 4 ml of dichloromethane, and the mixture is stirred at room temperature for one night.

It is then filtered, the residue is washed witch a small amount of dichloromethane, and the filtrate is concentrated. Chromatography of the residue on silica gel using 5:1 hexane/ethyl acetate and repeated chromatography on silica gel using dichloromethane and crystallization from hexane give 0.22 g (73% yield) of the desired product exhibiting the phase sequence: X 112 S$_A$ 195 I.

Example 4

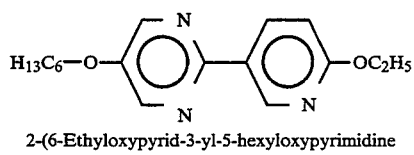

2-(6-Ethyloxypyrid-3-yl-5-hexyloxypyrimidine

Preparation of the ethyloxypyridinamidine hydrochloride and condensation with 2-benzyloxy-3-dimethylaminoacrolein are carried out analogously to Example 1.

0.22 g (1 mmol) of 5-hydroxy-2-(6-ethyloxypyrid-3-yl)pyrimidine is dissolved in 3 ml of DMF, and the resulting solution is added dropwise to 60 mg (2 mmol) of 80% NaH in 2 ml of DMF. 0.22 g (1.33 mmol) of bromohexane in 4 ml of DMF is then added dropwise, and the mixture is stirred at 60° C. for 2 hours. The reaction solution is poured into 10 ml of H$_2$O, the mixture is extracted 3 times with dichloromethane, the organic phases are washed with saturated NaCl solution and H$_2$O, dried with MgSO$_4$ and concentrated. The crude product is chromatographed on SiO$_2$ using 5:1 hexane/ethyl acetate and recrystallized from hexane.

X 69 S$_A$ 95 I

Example 5

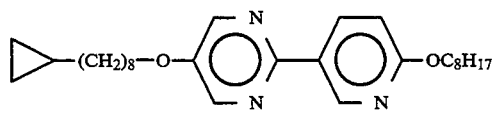

Analogously to Example 2, 5-hydroxy-2-(6-octyloxypyrid-3-yl)pyrimidine is reacted with 8-cyclopropylbromooctane to give 8-cyclopropyloctyl 2-(6-octyloxypyrid-3-yl)pyrimidine-5-yl ether

X 78 S$_C$ S$_A$ 85 I

Example 6

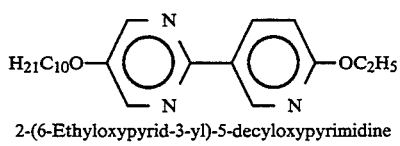

2-(6-Ethyloxypyrid-3-yl)-5-decyloxypyrimidine

Analogously to Example 5 from 5-hydroxy-2-(6-ethyloxypyrid-3-yl)pyrimidine and bromodecane

X 54 S$_A$ 100 I

Example 7

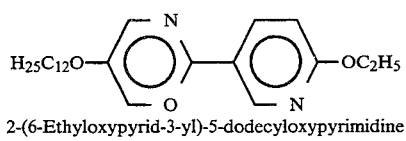

2-(6-Ethyloxypyrid-3-yl)-5-dodecyloxypyrimidine

Analogously to Example 5 from 5-hydroxy-2-(6-ethyloxy-pyrid-3-yl)pyrimidine and bromododecane

X 57 $S_A$ 98 I

Example 8

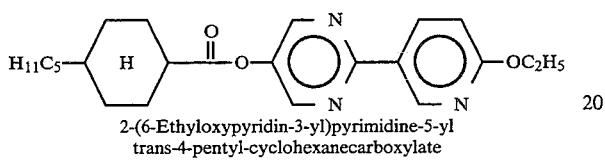

2-(6-Ethyloxypyridin-3-yl)pyrimidine-5-yl trans-4-pentyl-cyclohexanecarboxylate

Prepared analogously to Example 3 from 5-hydroxy-2-(6-ethyloxypyridin-3-yl)pyrimidine and trans-4-pentylcyclohexanecarboxylic acid

X 128 $S_A$ 199 N 210 I

Example 9

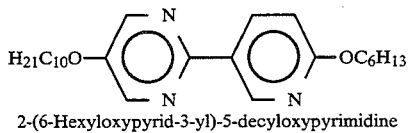

2-(6-Hexyloxypyrid-3-yl)-5-decyloxypyrimidine

Preparation of 6-hexyloxy-3-pyridineamidine hydrochloride and condensation with 2-benzyloxy-3-dimethylaminoacrolein are carried out analogously to Example 1, and alkylation of 5-hydroxy-2-(6-hexyloxypyridin-3-yl)pyrimidine is carried out analogously to Example 5. Finally, the product is recrystallized from heptane.

X 54 $S_C$ 82 $S_A$ 97 I

Example 10

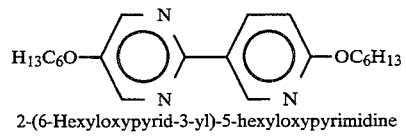

2-(6-Hexyloxypyrid-3-yl)-5-hexyloxypyrimidine

Prepared analogously to Example 9 from 5-hydroxy-2-(6-hexyloxypyridin-3-yl)pyrimidine and bromohexane.

X 48 $S_A$ 95 I

Example 11

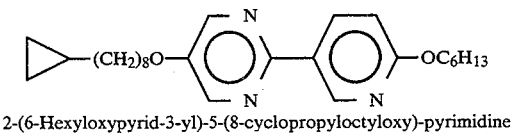

2-(6-Hexyloxypyrid-3-yl)-5-(8-cyclopropyloctyloxy)-pyrimidine

Prepared analogously to Example 9 from 5-hydroxy-2-(6-hexyloxypyridin-3-yl)pyrimidine and 8-cyclopropylbromooctane

X 58 $S_C$ 76 $S_A$ 85 I

Example 12

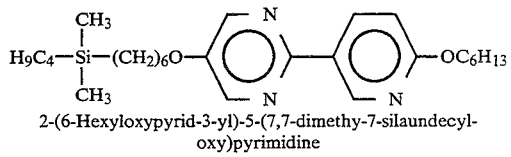

2-(6-Hexyloxypyrid-3-yl)-5-(7,7-dimethy-7-silaundecyloxy)pyrimidine

Prepared analogously to Example 9 from 5-hydroxy-2-(6-hexyloxypyridin-3-yl)pyrimidine and 7,7-dimethyl-7-silabromoundecane

X 24 $S_C$ 28 I N.N.

Example 13

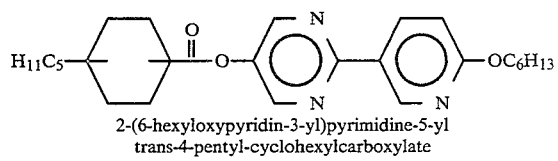

2-(6-hexyloxypyridin-3-yl)pyrimidine-5-yl trans-4-pentyl-cyclohexylcarboxylate

Prepared analogously to Example 8 from 5-hydroxy-2-(6-hexyloxypyridin-3-yl)pyrimidine and trans-4-pentylcyclohexanecarboxylic acid

X 114 $S_A$ 201 I

Example 14

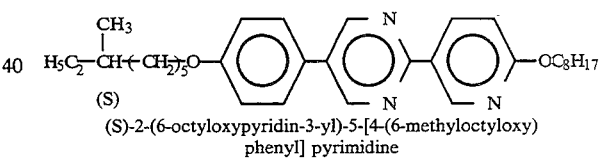

(S)-2-(6-octyloxypyridin-3-yl)-5-[4-(6-methyloctyloxy)phenyl] pyrimidine

Prepared analogously to Example 1 from 6-octyloxynicotinamidine hydrochloride and (S)-2-[4-(6-methyloctyloxy)phenyl]-1-dimethylamino-3-dimethylaminopropanoperchlorate.

X 76 $S_C^*$ 171 $S_A^*$ 180 I

Example 15

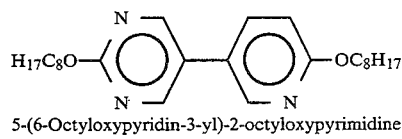

5-(6-Octyloxypyridin-3-yl)-2-octyloxypyrimidine

A solution of 7.2 g (55.3 mmol) of 1-octanol in 20 ml of DMF is added dropwise to a suspension of 1.38 g of NaH (80%) in 10 ml DMF which had been heated to 50° C. The reaction solution is heated at 80° C. for 90 minutes. A solution of 10 g (42 mmol) of 2,5-dibromopyridine in 35 ml of DMF is then added dropwise at this temperature. The reaction mixture is stirred at 80° C. for another 6 hours. The solution is poured onto 200 ml of ice water, the resulting mixture is extracted 4 times with dichloromethane, the combined organic phases are dried, and the solvent is distilled off. The product 2-octyloxy-5-bromopyridine is purified by chromatography on silica gel using 7:1 heptane/ethyl acetate.

Analogously to the above procedure, 5.95 g of 2,5-dibromopyrimidine are reacted with 7.9 g of 1-octanol to give 2-octyloxy-5-bromopyrimidine. The product is purified by chromatography on silica gel.

2.75 g (10 mmol) of 2-octyloxy-5-bromopyridine are dissolved in 60 ml of absolute diethyl ether, and the solution is cooled to −75° C. under inert gas. 16 mmol of 1.6M butyllithium solution in hexane are added, and the mixture is additionally stirred at −75° C. for 15 minutes. 4.5 g of triisopropylborate in 50 ml of absolute diethyl ether are then added dropwise. The cooling device is then removed. After the batch has warmed to room temperature, 50 ml of 10% HCl are added, and the mixture is additionally stirred at room temperature for 30 minutes. The phases are separated, and the organic phase is washed twice with saturated NaCl solution. The solvent is distilled off in vacuo, and the residue is recrystallized from acetonitrile, giving 6-octyloxypyridine-3-boronic acid.

1.36 g (5.42 mmol) of 6-octyloxypyridine-3-boronic acid and 1.30 g (4.52 mmol) of 2-octyloxy-5-bromopyrimidine are introduced with stirring into a mixture of 39 ml of benzene, 26 ml of ethanol and 13 ml of water. 1.15 g (10.85 mmol) of $Na_2CO_3$ and 50 mg of tetrakis(triphenylphosphine)palladium (0) are added with stirring. The reaction mixture is refluxed for 5 hours. Undissolved material is filtered off, the residue is washed with ethanol, and the solvent is removed from the filtrate. The product is purified by chromatography on silica gel.

X 64 $S_C$67 $S_A$91 I

Example 16

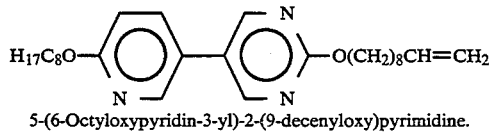

5-(6-Octyloxypyridin-3-yl)-2-(9-decenyloxy)pyrimidine.

Prepared analogously to Example 15 from 2-(9-decenyloxy)-5-bromopyridine and 6-octyloxypyridine-3-boronic acid.

X 60 $S_C$65 $S_A$80 I N.N.

Example 17

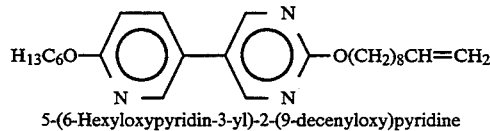

5-(6-Hexyloxypyridin-3-yl)-2-(9-decenyloxy)pyridine

Prepared analogously to Example 15 from 2-(9-decenyloxy)-5-bromopyrimidine and 6-hexyloxypyridine-3-boronic acid.

X 53 $S_A$81 I N.N.

Use Example 1
Ferroelectric liquid crystal mixture

A ferroelectric mixture comprising the components

| | |
|---|---|
| 5-octyloxy-2-(4-hexyloxyphenyl)pyrimidine | 22.8 mol % |
| 5-octyloxy-2-(4-butyloxyphenyl)pyrimidine | 24 mol % |
| 5-octyloxy-2-(4-decyloxyphenyl)pyrimidine | 19.2 mol % |
| 5-octyloxy-2-(4-octyloxyphenyl)pyrimidine | 10.5 mol % |
| 4'-(5-decylpyrimidine-2-yl)phenyl trans-4-pentylcyclohexanecarboxylate | 13.5 mol % |
| (2S,3S)-3-butyloxiran-2-ylmethyl 2-(6-octyloxypyrid-3-yl)pyrimidin-5-yl ether | 10 mol % | is prepared. It exhibits the following liquid-crystalline phase ranges:

$S_C$*81 $S_A$*98 N*103 I and has a spontaneous polarization of 6.8 nC/cm at a temperature of 20° C. and a switching time of 250 μs at a field strength of 10 V/μm.

Comparative Example III

Compared with the above mixture, the liquid-crystalline mixture described in DE 3,831,226.3, which only differs from the abovementioned mixture by not containing (2S,3S)-3-butyloxiran-2-ylmethyl 2-(6-octyloxypyrid-3-yl)pyrimidine-5-yl ether, exhibits the following phase ranges:

$S_C$*84 $S_A$*93N*105 I

The addition of the compound according the invention leads to a broadening of the $S_A$* phase range.

This example documents that the compounds according to the invention are suitable for use in ferroelectric mixtures because, inter alia, as doping substances they lead to short switching times. Moreover, these components are highly compatible with phenylpyrimidines.

Use Example 2

A binary mixture comprising
A 45 mol % of 2-(4-octyloxyphenyl)pyrimidine-5-yl heptanoate (phases sequence: X 69 $S_C$65 N 89 I) and B 55 mol % of the compound according to the invention: 2-(octyloxypyridin-5-yl)octyloxypyrimidine is prepared. It exhibits the phases:

X 62 $S_C$ 71 $S_A$ 85 N 88 I

The addition of the compound (B) according to the invention leads to an improved mixture having a lower melting point.

Moreover, in contrast to the starting component (A), this mixture exhibits an $S_A$ phase which, in ferroelectric mixtures, is necessary for good orientation of the mixture when filling the display. Surprisingly, the novel compounds according to the invention are capable of inducing an $S_A$ phase in the mixtures.

Use Example 3

A binary mixture comprising:
C 62.5 mol % of 2-(4-octyloxyphenyl)pyrimidin-5-yl heptanoate and (phase sequence: X 69 $S_C$ 65 N 89 I)

D 37.5 mol % of the compound according to the invention: 2-(octyloxypyridin-5-yl)-5-octyloxypyrimidine is prepared.

It exhibits the phases:

X 54 $S_C$ 70 N 91 I

The addition of the compound (D) according to the invention leads to an improved mixture having a substantially lower melting point.

The compounds according to the invention are particularly suitable for lowering the melting point in a mixture with phenylpyrimidines.

Use Example 4

A liquid crystal mixture comprising the components

| | |
|---|---|
| 5-octyl-2-(4-hexyloxyphenyl)pyrimidine | 20.9 mol % |
| 5-octyl-2-(4-decyloxyphenyl)pyrimidine | 13.9 mol % |
| 5-decyl-2-(4-hexyloxyphenyl)pyrimidine | 13.6 mol % |
| 5-octyl-2-(4'-(7''-cyclopropylheptyloxy)-phenyl)pyrimidine | 11.4 mol % |
| 5-octyl-2-(4'-(6''-cyclopropylhexylcarbonyloxy)phenyl)pyrimidine | 14.0 mol % |
| 5-(8'''-cyclopropyloctyloxy)-2-(4'-(4''-trans-pentylcyclohexyl)phenyl)pyrimidine | 16.2 mol % |
| 2-(6-hexyloxypyrid-3-yl)-5-(8-cyclopropyloctyloxy)pyrimidine | 10.0 mol % | exhibits the following liquid-crystalline phase ranges:

X−10.6 $S_C$ 62 $S_A$ 77 N 81 I

Compared with the above mixture, the liquid-crystalline mixture which only differs from the abovementioned mixture by not containing the latter compound (according to the invention), exhibits

X−0.5 $S_C$ 63 $S_A$ 72 N 81 I

The addition of the compound according to the invention leads to a lowering of the melting point. The broadening of the $S_A$ phase facilitates orientation of the liquid crystal mixture in an electrooptical display element.

Use Example 5

A liquid crystal mixture comprising the components

| | |
|---|---|
| 5-octyl-2-(4-hexyloxyphenyl)pyrimidine | 14.6 mol % |
| 5-octyl-2-(4-decyloxyphenyl)pyrimidine | 9.7 mol % |
| 5-decyl-2-(4-hexyloxyphenyl)pyrimidine | 9.4 mol % |
| 5-octyl-2-(4'-(7''-cyclopropylheptyloxy) phenyl)pyrimidine | 7.9 mol % |
| 5-octyl-2-(4'-(6''cyclopropylhexylcarbonyloxy phenyl)pyrimidine | 9.8 mol % |
| 5-(8'''-cyclopropyloctyloxy)-2-(4'-(4''-trans-pentylcyclohexyl)phenyl)pyrimidine | 11.3 mol % |
| 4'-(5-(8'''-cyclopropyloctyl)pyrimidin-2-yl)phenyl trans-4-pentylcyclohexanecarboxylate | 7.0 mol % |
| 5-(5''-cyclopropylpentyloxy)-2-(4'-hexyloxyphenyl)pyrimidine | 10.4 mol % |
| 2-(4'-hexylphenyl)-5-(4''-(4'''-cyclopropylbutyloxy)phenyl)pyrimidine | 9.9 mol % |
| 5-(6-octylpyridin-3-yl)-2-(9-decenyloxy)-pyrimidine | 10.0 mol % | exhibits the following liquid-crystalline phase ranges:

X−7 $S_c$ 69 $S_A$ 84 N 93 I

Use Example 6

A liquid crystal mixture comprising the components

| | |
|---|---|
| 5-octyl-2-(4-hexyloxyphenyl)pyrimidine | 14.6 mol % |
| 5-octyl-2-(4-decyloxyphenyl)pyrimidine | 9.7 mol % |
| 5-decyl-2-(4-hexyloxyphenyl)pyrimidine | 9.4 mol % |
| 5-octyl-2-(4'-(7''-cyclopropylheptyloxy) phenyl)pyrimidine | 7.9 mol % |
| 5-octyl-2-(4'-(6''cyclopropylhexylcarbonyloxy) phenyl)pyrimidine | 9.8 mol % |
| 5-(8'''-cyclopropyloctyloxy)-2-(4'-(4''-trans-pentylcyclohexyl)phenyl)pyrimidine | 11.3 mol % |
| 4'-(5-(8'''-cyclopropyloctyl)pyrimidin-2-yl)phenyl trans-4-pentylcyclohexanecarboxylate | 7.0 mol % |
| 5-(5''-cyclopropylpentyloxy)-2-(4'-hexyloxyphenyl)pyrimidine | 10.4 mol % |
| 2-(4'-hexylphenyl)-5-(4''-(4'''-cyclopropylbutyloxy)phenyl)pyrimidine | 9.9 mol % |
| 5-(6-octyloxypyridine-3-yl)-2-octyloxypyrimidine | 10.0 mol % | exhibits the following liquid-crystalline phase ranges:

X−7 $S_C$ 69 $S_A$ 83 N 94 I

A liquid crystal mixture which only differs from the two last-mentioned mixtures by not containing the last compound according to the invention exhibits the phase ranges:

X−4 $S_C$ 72 $S_A$ 80 N 96 I

The addition of the compound according to the invention, apart from leading to a lowering of the melting point, results in an advantageous broadening of the $S_A$ phase range.

Use Example 7

A mixture comprising the components

| | |
|---|---|
| 5-heptyl-2-(4-pentyloxyphenyl)pyrimidine | 13.8 mol % |
| 5-heptyl-2-(4-heptyloxyphenyl)pyrimidine | 9.2 mol % |
| 5-heptyl-2-(4-butyloxyphenyl)pyrimidine | 14.8 mol % |
| 5-(6''-cyclopropylhexyloxy)-2-(4'-octyloxyphenyl)pyrimidine | 14.0 mol % |
| (trans-4-pentylcyclohexylmethyloxy)-5-(8''-cyclopropyloctyloxy)pyrimidin-2-yl-phenyl [sic] | 6.4 mol % |
| 5-(8''-cyclopropyloctyl)pyrimidin-2-yl-phenyl trans-4-pentylcyclohexanecarboxylate | 11.1 mol % |
| 5-octyl-2-(4'-(6''-cyclopropylhexyl-carbonyloxy)phenyl)pyrimidine | 20.7 mol % |
| 2-(6-hexyloxypyrid-3-yl)-S-hexyloxy-pyrimidine | 10.0 mol % | exhibits the following liquid-crystalline phase ranges:

X 2.1 $S_C$ 54 $S_A$ 73 N 91 I compared with the above mixture, the liquid-crystalline mixture which only differs from the abovementioned mixture by not containing a compound according to the invention exhibits the following phase ranges:

X 3.4 $S_C$ 61 N 92 I

This comparison shows that the addition of even a small amount of the compound according to the invention can produce an $S_A$ phase in liquid-crystalline mixtures while simultaneously lowering the melting point.

What is claimed is:

1. A pyridylpyrimidine compound of the formula I

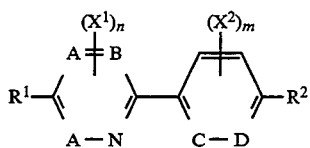

in which

A is N and B is CH or A is CH and B is N,
C is N and D is CH or C is CH and D is N,
R¹ is straight-chain or branched (chiral or achiral) alkyl having 1 to 16 carbon atoms or alkenyl having 2 to 16 carbon atoms, it also being possible for one or two non-adjacent —CH₂— groups to be replaced by —O—, —S—, —CO—, —CO—O—, —O—CO— or —O—CO—O— and it also being possible for one H to be replaced by F, or is one of the following radicals OCF₃, OCHF₂,

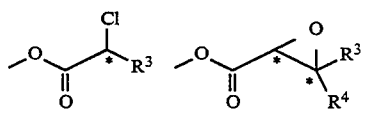

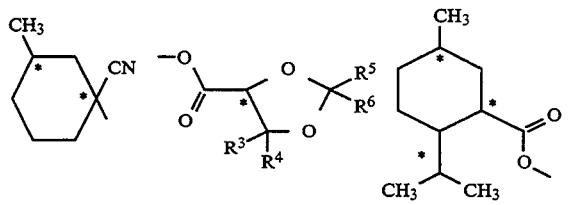

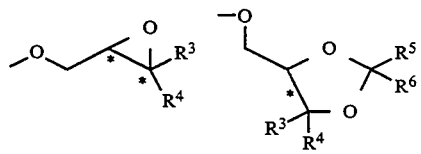

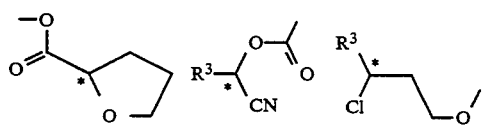

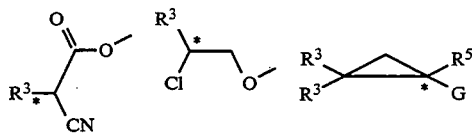

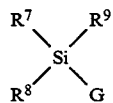

or R¹⁰—E—M—, with the proviso that if A is N, must not be R¹ must not be linked with the pyrimidine via a —CO—O— or O—CO—O— group, R² is identical to R¹, with the proviso that if D is N, the radicals R¹ linked to the pyridine ring via an O—CO— or an —O—CO—O— group are excluded, X¹, X² are F, Cl, CN, n,m, identical or different, are zero, 1 or 2, R³, R⁴, R⁵, R⁶ are H, straight-chain or branched alkyl having 1 to 16 carbon atoms or alkenyl with 2 to 16 carbon atoms, in which a —CH₂— group not adjacent to the linkage point can also be replaced by —O—, —CO—O— or —O—CO— or R³ and R⁴ or R⁵ and R⁶ together are cyclic alkyl having 3 to 8 carbon atoms, R⁷, R⁸, R⁹ are straight-chain or branched alkyl having 1 to 16 carbon atoms or alkenyl having 2 to 16 carbon atoms, in which one or two non-adjacent —CH₂— groups can also be replaced by —O—, —CO—O— or —O—CO—, with the proviso that silicon is only bound to a carbon which has hydrogen and/or carbon as neighboring atoms, or are cyclic alkyl having 3 to 8 carbon atoms, or together with silicon can also be

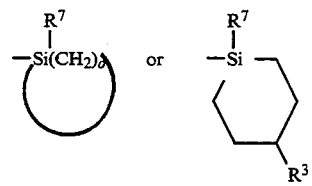

G is straight-chain or branched alkylene having 1 to 16 carbon atoms or alkenylene having 2 to 16 carbon atoms, in which one or two non-adjacent —CH₂— groups can also be replaced by —O—, —S—, —O—CO—, —CO—O—, —S—CO— or —CO—S—, R¹⁰ is identical to R¹ but is not R¹⁰—E—M and without the abovementioned proviso for R¹, E is 1,4-phenylene in which 1 or 2 H can also be replaced by F, Cl and/or CN, trans-1,4-cyclohexylene in which 1 or 2 H can also be replaced by F, Cl, CN and/or CH₃, pyrazine-2,5-diyl, pyridazine-3,6-diyl, pyridine-2,5-diyl, pyrimidine-2,5-diyl, 1,3,4-thiadiazole-2,5-diyl, 1,3-dioxane-2,5-diyl or 1,3-dithiane-2,5-diyl;

M is —CO—O—, —O—CO—, —CO—S—, —S—CO—, —CH₂O—, —O—CH₂—, —C≡C, —CH═CH— or a single bond, o is an integer from 3 to 8.

2. A pyridylpyrimidine as claimed in claim 1, wherein in the formula (I) R¹ and R², identical or different, are linear or branched alkyl, alkyloxy or alkyldimethylsilylalkyl(oxy) or one of the chiral substituents listed in claim 1.

3. A pyridylpyrimidine as claimed in claim 1, having the formula (II), (III) or (IIIa),

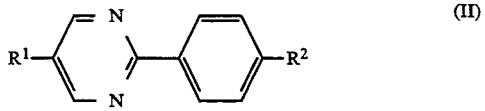

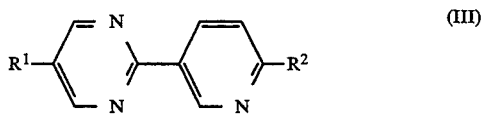

-continued

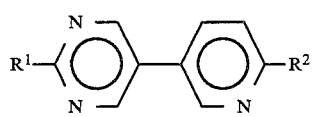
(IIIa)

$R^1$ and $R^2$ having the meanings given in claim 1.

4. A liquid crystalline mixture composed of at least two components, wherein the mixture contains at least one pyridylpyrimidine compound of the formula (I) as claimed in claim 1.

5. A liquid-crystalline mixture as claimed in claim 4, which is ferroelectric.

6. A liquid-crystalline mixture as claimed in claim 4, which is nematic.

* * * * *

UNITED STATES PATENT AND TRADEMARK OFFICE
CERTIFICATE OF CORRECTION

PATENT NO. : 5,443,754            Page 1 of 2
DATED : August 22, 1995
INVENTOR(S) : Escher et al.

It is certified that error appears in the above-indentified patent and that said Letters Patent is hereby corrected as shown below:

IN THE ABSTRACT:

In the structural formula (1) of the pyridylpyrimidine compound, change " ≫A-N≪ " to -- ≫A-B≪ --.

IN THE CLAIMS:

Column 17, lines 5-10, in claim 1, structural formula (I), change " ≫A-N≪ " to -- ≫A-B≪ --.

UNITED STATES PATENT AND TRADEMARK OFFICE
CERTIFICATE OF CORRECTION

PATENT NO. : 5,443,754
DATED : August 22, 1995
INVENTOR(S) : Escher, et al

It is certified that error appears in the above-indentified patent and that said Letters Patent is hereby corrected as shown below:

Column 17, line 61, after "A is N", delete "must not be".

Signed and Sealed this

Sixteenth Day of April, 1996

BRUCE LEHMAN

*Attest:*

*Attesting Officer*  Commissioner of Patents and Trademarks